United States Patent
Sarfaty

(10) Patent No.: US 6,855,569 B1
(45) Date of Patent: Feb. 15, 2005

(54) CURRENT LEAKAGE MEASUREMENT

(75) Inventor: Moshe Sarfaty, Cupertino, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/719,570

(22) Filed: Nov. 21, 2003

(51) Int. Cl.$^7$ .................... H01L 21/00; G01R 31/305
(52) U.S. Cl. .................................. 438/17; 324/751
(58) Field of Search ................... 438/10, 11, 14, 438/17, 18; 324/501, 512, 537, 750, 751, 765, 766, 769, 557–559

(56) References Cited

PUBLICATIONS

M. Ceschia et al., "Low Field Leakage Current and Soft Breakdown in Ultra–Thin gate Oxides After Heavy Ions, Electrons or X–ray Irradiation," Jun. 2000, IEEE Transactions on Nuclear Science, pp. 566–573.*

* cited by examiner

Primary Examiner—Evan Pert
(74) Attorney, Agent, or Firm—Luedeka, Neely & Graham, P.C.

(57) ABSTRACT

A method for detecting current leakage of a film on a substrate. The film is repeatedly irradiated with an electron beam, thereby causing the film to emit x-rays. The emitted x-rays are detected with an x-ray detector, the detected x-rays emitted with each repeated irradiation of the film are counted to produce an x-ray count rate. The trend of the x-ray count rate is determined, and the current leakage of the film is determined from the trend of the x-ray count rate.

20 Claims, 3 Drawing Sheets

CURRENT LEAKAGE MEASUREMENT

This invention relates to the field of integrated circuit fabrication. More particularly, this invention relates to testing electrical properties of integrated circuits.

BACKGROUND

Modern integrated circuits, such as monolithic semiconductor devices formed of materials such as group IV materials like silicon and germanium and group III–IV materials such as gallium arsenide, and combinations of such materials, are typically comprised of millions of transistor devices. The transistor devices vary in many different aspects, but generally have a channel disposed between a source region and drain region, with a gate electrode disposed over the channel. The channel and the gate are separated by a relatively thin layer of a non electrically conductive material, commonly called the gate insulation layer.

Silicon dioxide has typically been used as the dielectric material between the electrically conductive gate electrode, often formed of polysilicon, and the semiconducting channel of the transistor. Silicon dioxide has provided adequately high capacitance for gate insulation in the past, with devices having gate geometries of about 130 nanometers and greater.

Current transistor geometries use a gate insulation layer of silicon dioxide that is about ten to about thirty angstroms thick, or the thickness of about five to about twenty individual silicon atoms. The silicon dioxide layer gates the electrons through the channel, controlling the flow of electricity across the transistor. However, when the transistor is reduced in size, the silicon dioxide gate insulation layer is also proportionally thinned. As gate lengths decrease from one hundred and thirty nanometers to ninety, sixty-five, and even thirty nanometers, the thickness of the silicon oxide gate will be reduced to less than ten angstroms, or to about three monolayers.

Unfortunately, as the gate insulation layer is reduced to less than about twenty angstroms, the silicon dioxide tends to have difficulty in providing effective insulation from the effects of quantum tunneling currents, and the transistor tends to exhibit relatively high leakage. Thus, current leakage is a major concern in ultra-thin dielectric gates used in the transistor devices of integrated circuits.

The existing methods of measuring current leakage in gates are performed on non production substrates, or in other words, substrates which do not include integrated circuits intended for sale. These methods typically cannot be performed on production substrates, because they require a relatively large surface area of the gate material in order to test the leakage, and modern integrated circuits use gates that are smaller than the area required by the test methods. Thus, such tests are typically performed on layers of the gate insulation material that are formed into special, larger test structures, which are disposed on special test substrate. While such test structures could be formed on standard production substrates, they would tend to require a lot of surface area that could otherwise be used for production integrated circuits.

One method of testing leakage current is accomplished by using a contact probe and a current-voltage method, which is destructive to the structure being tested. Thus, not only is a relatively large gate layer required, but the gate layer is damaged by the test. Another method of testing current leakage is a corona oxide characterization of semiconductor, which is a non-contact method that deposits a charge on the gate dielectric and measures with a close proximity probe tip the decay in the surface voltage over time. This method also requires a relatively large test area, and thus is used on non production substrates only.

Therefore, there are many disadvantages to the old methods, including the destructive nature of the contact measurement method, and the relatively large spot size which reduces the ability of the methods to take readings on small gate dielectrics, and which therefore limits the traditional measurement methods to only non production substrates and structures.

What is needed, therefore, is a method of measuring current leakage that overcomes or reduces some of these or other problems.

SUMMARY

The above and other needs are met by a non destructive, non contact method for detecting current leakage of a film on a substrate. The film is repeatedly irradiated with an electron beam, thereby causing the film to emit x-rays. The emitted x-rays are detected with an x-ray detector, and the detected x-rays emitted with each repeated irradiation of the film are counted to produce an x-ray count rate. The trend of the x-ray count rate is determined, and the current leakage of the film is determined from the trend of the x-ray count rate.

In this manner, current leakage can be determined on the standard gate dielectric layers of production die, because the electron beam is small enough to be directed at a very tiny structure. Further, the electron beam does not damage the gate dielectric layer, and so the integrated circuit is not destroyed during the test.

In various embodiments, a trend of decreasing x-ray count rates indicates a relatively low current leakage of the film, and a trend of stable x-ray count rates indicates a relatively high current leakage of the film. The substrate is preferably a monolithic semiconductor integrated circuit production substrate. Preferably, the film is a gate dielectric film, and is most preferably a gate dielectric film in a transistor of a production integrated circuit. The electron beam and the x-ray detector are preferably provided by a spectrometer of a type used for determining the elemental composition of the film. In some embodiments the film is between about ten angstroms and about thirty angstroms in thickness, and is formed of silicon oxide. The method is preferably accomplished as part of an integrated circuit fabrication process. In various embodiments, the x-rays are detected at one or more of a nitrogen band energy level and at an oxygen band energy level. In some embodiments the trend of the x-ray count rate is observed while varying the irradiation pulse time and the inter-pulse wait time of the electron beam. Preferably, the landing energy is kept below about two and one half times the observed photon energy.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIG. 2 is a graph of W12–W15 with thicknesses of 11.7 angstroms, 12.5 angstroms, 15.0 angstroms, and 16.5 angstroms, respectively, and N-Doses of 0.97E15, 1.22E15, 1.33E15, 1.38E15 atoms per square centimeter, respectively. The change in N-Dose and thickness affects the gate leakage. The thicker and higher N-Dose films show less leakage than the thinner and lower N-Dose films.

Figure 3:
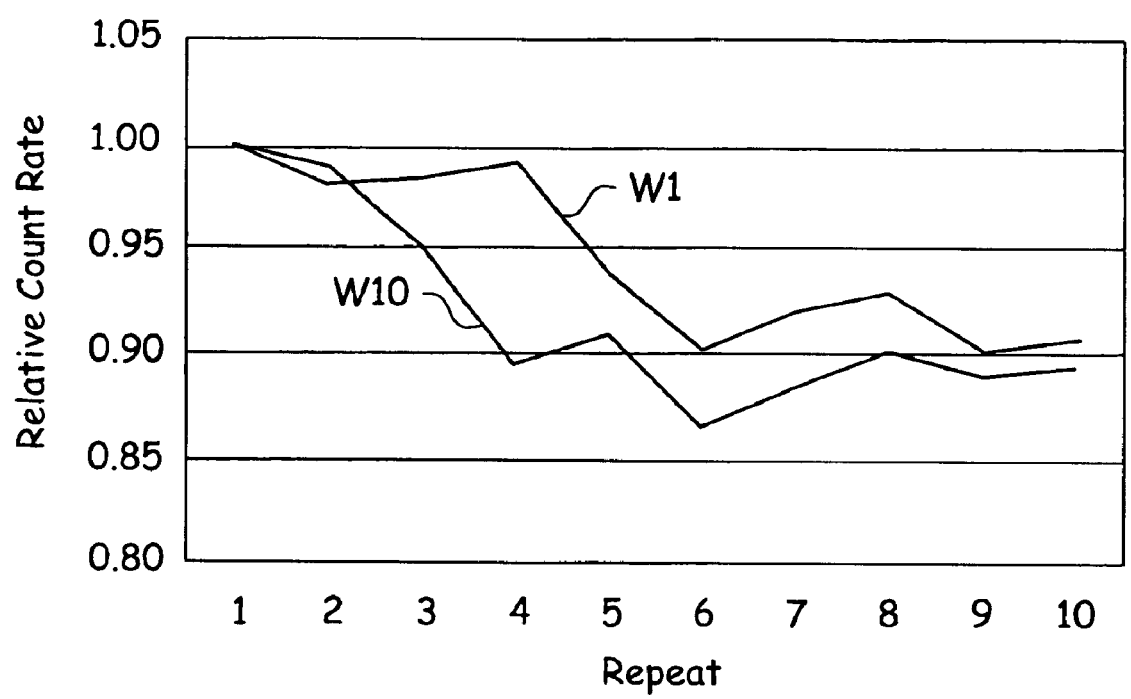

FIG. 3 is a graph of W1 and W10 with an N-Dose of 2.44E15 and 3.56E15 atoms per square centimeter, respectively, and similar thicknesses of about 16.5 angstroms. The higher the N-Dose the lower the leakage.

DETAILED DESCRIPTION

One purpose of the various embodiments of the invention is to measure and characterize gate dielectric current leakage on a production substrate using a non contact and non destructive method.

The preferred embodiments of the invention make use of a highly controlled and spatially focused electron beam and x-ray detector. Currently such equipment is commonly used to measure the elemental composition of gate dielectric and other layers, such as nitrogen and oxygen content. However, other equipment that enables the measurement of x-ray emission can alternately be used for the measurements as described herein. By repeatedly or continually monitoring x-ray measurements at a given site, a gate dielectric current leakage can be detected.

It has been determined that there is generally a decline in x-ray counts when the gate is charged. Without being bound by theory, it is believed that this is due to a change in the landing energy of the electron beam. This in turn effects the excitation efficiency of the species in the film that is so irradiated. When the gate leakage is high, the charging of the gate dielectric tends to dissipate relatively quickly, and tends to be at a relatively low level, and the change in the x-ray intensity from exposure to exposure is minimal, such as within the measurement noise of the system. Therefore, very little if any change in the x-ray count rate is detected over time.

However, when the gate leakage is low, the charging of the gate dielectric tends to last for a longer time and tends to be at a relatively high level, and the charge accumulation tends to increase with every repeated exposure, and the landing energy tends to further decrease. The decrease in the apparent landing energy due to charge accumulation tends to reduce the x-ray count rates. Thus, when the x-ray decay is higher, or in other words when the x-ray count rate decreases over time, it is an indication that the charge accumulation is also higher, and is further an indication that the degree of leakage in the gate dielectric is less.

To improve the sensitivity of the method to the local charging of the dielectric layer, the selected landing energy is preferably optimized such that the sensitivity to the change in the energy on the observed x-ray count rate decay is higher. At landing energies below the optimal excitation energy, which is about two and one-half times the observed photon energy, the change in the electron excitation cross section is fairly steep, which makes it much more sensitive to landing energy changes, and therefore more sensitive to any charge that is remaining on the dielectric layer.

Figure 1:
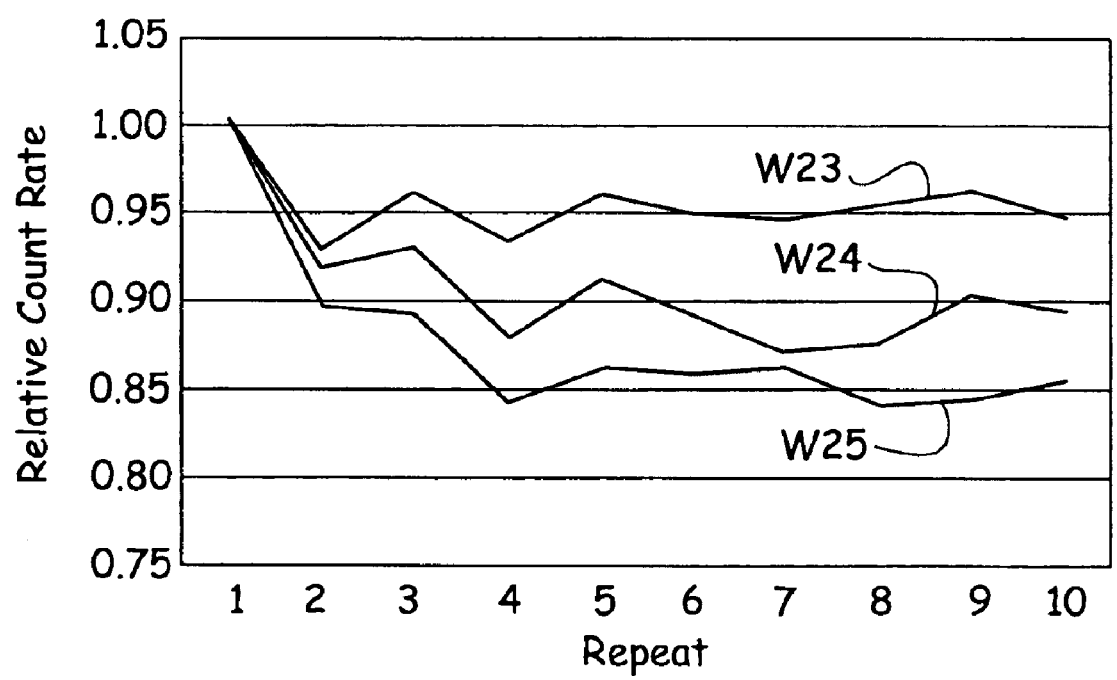
FIG. 1 is a graph of W23–W25 with an N-Dose of 0.9E15, 1.66E15, 2.47E15 atoms per square centimeter, respectively, and similar thickness of about 27 angstroms. The higher the N-Dose the lower the leakage.
Figure 2:
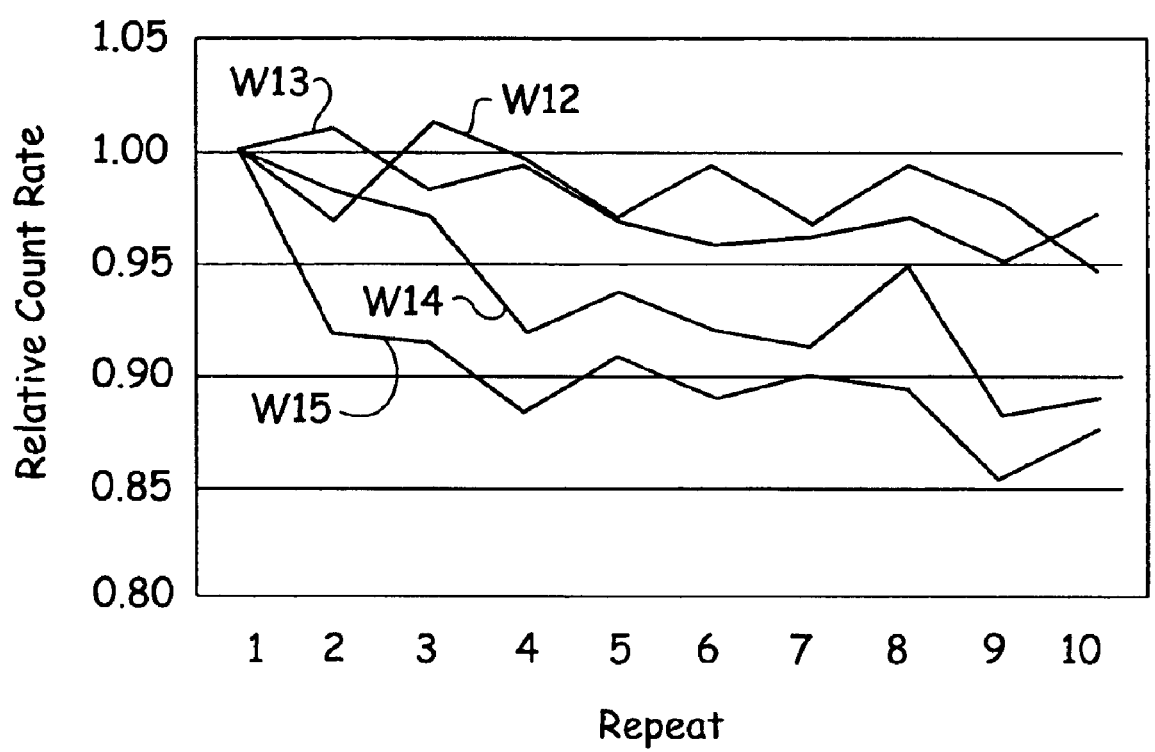

The results of several substrate tests having different gate oxide thicknesses and different amounts of nitrogen in the gate dielectric are given in FIGS. 1–3. The indication to is that with a higher nitrogen content, such as can be measured by a MetriX nitrogen spectrometer, a relatively greater x-ray count rate decay is observed, thereby generally indicating less current leakage. The thinner and lower nitrogen containing films exhibit less of a signal decay, thereby generally suggesting higher current leakage in these cases.

FIG. 1 depicts a graph of films identified as W23–W25, with N-Doses of 0.9E15, 1.66E15, 2.47E15 atoms per square centimeter, respectively, and similar thicknesses of about 27 angstroms. As can be seen in the graph, the higher the N-Dose the lower the leakage. FIG. 2 depicts a graph of films identified as W12–W15, with thicknesses of 11.7 angstroms, 12.5 angstroms, 15.0 angstroms, and 16.5 angstroms, respectively, and N-Doses of 0.97E15, 1.22E15, 1.33E15, 1.38E15 atoms per square centimeter, respectively.

The change in N-Dose and thickness affects the gate leakage. As can be seen, the thicker and higher N-Dose films show less leakage than the thinner and lower N-Dose films. FIG. 3 depicts a graph of films identified as W1 and W10, with N-Doses of 2.44E15 and 3.56E15 atoms per square centimeter, respectively, and similar thicknesses of about 16.5 angstroms. As can be seen, the higher the N-Dose the lower the leakage.

Preferably, the exposure time of the e-beam is changed, as well as the interval between exposures, and the change in the x-ray count rates is then observed. The change in x-ray count rates is related to the effective landing energy, thereby enabling the determination of the surface voltage. Also, the amount of charge introduced is preferably tightly controlled by measuring the gun current and exposure time. Knowing the effect on the surface voltage through landing energy modeling for the measured x-ray decay, yields the change in charge with time as a result of the leakage current.

In the examples described herein, the nitrogen line is used to measure both the N-dose in the film and the current leakage at the same time. In other embodiments, an oxygen spectrometer is also used, which provides another x-ray detection element for the gate dielectric layers. The oxygen count rates, together with the nitrogen count rates, tend to improve the accuracy of the measurement of the change in landing energy, and thereby the remaining charge on the gate dielectric layer.

One major advantage of the methods according to the preferred embodiments of the present invention is that they can be used on production substrates. This is possible because these methods can be implemented on a very small spot size, such as the size of the gates of actual production devices, and can be easily combined with compositional analysis of the ultra thin gate films. Further, these methods measure the current leakage in gate dielectrics without contacting the films, and without damaging the films in any way.

Thus, it is a novel aspect of the present invention to use the decay of x-ray count rates over time to measure the surface charge of a gate dielectric layer, and thereby to determine the current leakage of the gate dielectric layer. X-ray counts are typically averaged over time and repeated to provide elemental analysis information. However, in the current embodiments of the invention, the repeats are used to quantify the surface charge, which relates to the ability of the gate dielectric to maintain its charge, which is related to the current leakage.

Preferably an existing system, such as a MetriX, is used to collect x-ray counts over several repeats, and then the signal decay is used to calculate and determine the current leakage rate through the gate dielectric. The gate dielectric may have thickness variations and N-dose variations, both of which effect the gate leakage. However, using the x-ray counts of the first measurement iteration, the dose of nitrogen can be determined, and then the leakage of the gate dielectric can be measured from the repeated x-ray count rates. Thus, a clear pass or fail leakage criterion can be monitored on a production substrate, which has major importance for gate process control.

Current leakage of gate dielectrics, especially ultra-thin gate dielectrics, as well as future metal oxide gates and capacitors, is one of the key parameters that determines the performance of the gate. As described herein, a well established metrology method using an electron beam to excite x-rays of the gate dielectric film is used to directly monitor the current leakage of the actual gate dielectrics on production substrates. This measurement can be performed and used for in line process monitoring at a relatively high throughput, to very quickly capture process excursions or process drifts that may have major impact on the yields of the integrated circuits so produced. It can be implemented as part of the front end of line process monitoring. An early detection of process drift or excursion can potentially prevent or reduce yield loss, loss of process and tool time, and loss of materials.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A non destructive, non contact method for detecting current leakage of a film on a substrate, the method comprising the steps of:
   repeatedly irradiating the film with an electron beam, thereby causing the film to emit x-rays,
   detecting the emitted x-rays with an x-ray detector,
   counting the detected x-rays emitted with each repeated irradiation of the film to produce an x-ray count rate,
   determining a trend of the x-ray count rate, and
   determining the current leakage of the film from the trend of the x-ray count rate.

2. The method of claim 1, wherein a trend of decreasing x-ray count rates indicates a relatively low current leakage of the film.

3. The method of claim 1, wherein a trend of stable x-ray count rates indicates a relatively high current leakage of the film.

4. The method of claim 1, wherein the substrate is a monolithic semiconductor integrated circuit production substrate.

5. The method of claim 1, wherein the film is a gate dielectric film.

6. The method of claim 1, wherein the film is a gate dielectric film in a transistor of a production integrated circuit.

7. The method of claim 1, wherein the electron beam and the x-ray detector are provided by a spectrometer of a type used for determining elemental composition of the film.

8. The method of claim 1, wherein the film is between about ten angstroms and about thirty angstroms in thickness.

9. The method of claim 1, wherein the film is formed of silicon oxide.

10. The method of claim 1, wherein the method is accomplished as part of an integrated circuit fabrication process.

11. The method of claim 1, wherein the x-rays are detected at a nitrogen band energy level.

12. The method of claim 1, wherein the x-rays are detected at an oxygen band energy level.

13. The method of claim 1, wherein the x-rays are detected at both a nitrogen band energy level and an oxygen band energy level.

14. The method of claim 1, wherein the trend of the x-ray count rate is observed while varying an irradiation pulse time and an inter-pulse wait time of the electron beam.

15. The method of claim 1, wherein landing energy is kept below about two and one half times an observed photon energy.

16. A non destructive, non contact method for detecting current leakage of a gate dielectric film in a transistor on a monolithic semiconductor integrated circuit production substrate, the method comprising the steps of:
   repeatedly irradiating the film with an electron beam, thereby causing the film to emit x-rays,
   detecting the emitted x-rays with an x-ray detector,
   counting the detected x-rays emitted with each repeated irradiation of the film to produce an x-ray count rate,
   determining a trend of the x-ray count rate, and
   determining the current leakage of the film from the trend of the x-ray count rate.

17. The method of claim 16, wherein a trend of decreasing x-ray count rates indicates a relatively low current leakage of the film, and a trend of stable x-ray count rates indicates a relatively high current leakage of the film.

18. The method of claim 16, wherein the electron beam and the x-ray detector are provided by a spectrometer of a type used for determining elemental composition of the film.

19. The method of claim 16, wherein the x-rays are detected at both a nitrogen band energy level and an oxygen band energy level.

20. A non destructive, non contact method for detecting current leakage of a gate dielectric film in a transistor on a monolithic semiconductor integrated circuit production substrate, the method comprising the steps of:
   repeatedly irradiating the film with an electron beam, thereby causing the film to emit x-rays,
   detecting the emitted x-rays with an x-ray detector, wherein the electron beam and the x-ray detector are provided by a spectrometer of a type used for determining elemental composition of the film, and the x-rays are detected at both a nitrogen band energy level and an oxygen band energy level,
   counting the detected x-rays emitted with each repeated irradiation of the film to produce an x-ray count rate,
   determining a trend of the x-ray count rate, and
   determining the current leakage of the film from the trend of the x-ray count rate,
   wherein a trend of decreasing x-ray count rates indicates a relatively low current leakage of the film, and a trend of stable x-ray count rates indicates a relatively high current leakage of the film.

* * * * *